US008866608B2

(12) United States Patent
Balinski et al.

(10) Patent No.: US 8,866,608 B2
(45) Date of Patent: Oct. 21, 2014

(54) FACILITY SANITIZATION MANAGEMENT

(75) Inventors: Peter A. Balinski, Elmhurst, NY (US); John G. Musial, Newburgh, NY (US); Sandeep R. Patil, Pune (IN); Riyazahamad M. Shiraguppi, Pune (IN)

(73) Assignee: International Business Machines Corporation, Armonk, NY (US)

( * ) Notice: Subject to any disclaimer, the term of this patent is extended or adjusted under 35 U.S.C. 154(b) by 126 days.

(21) Appl. No.: 13/566,198

(22) Filed: Aug. 3, 2012

(65) Prior Publication Data

US 2014/0022074 A1    Jan. 23, 2014

Related U.S. Application Data

(63) Continuation of application No. 13/554,600, filed on Jul. 20, 2012.

(51) Int. Cl.
*G08B 1/08* (2006.01)
*G08G 1/00* (2006.01)

(52) U.S. Cl.
CPC ............................. *G08G 1/00* (2013.01)
USPC ............ 340/539.13; 340/539.12; 340/539.26; 340/572.1; 340/572.4; 340/572.8; 340/540; 340/541

(58) Field of Classification Search
CPC ................................. G08G 1/00; A16B 5/0084
USPC ............... 340/539.13, 539.12, 539.26, 571.1, 340/572.1–572.8, 540, 541
See application file for complete search history.

(56) References Cited

U.S. PATENT DOCUMENTS

| | | | |
|---|---|---|---|
| 6,236,317 B1 | 5/2001 | Cohen et al. | |
| 7,015,816 B2 | 3/2006 | Wildman et al. | |
| 7,551,092 B1 * | 6/2009 | Henry | 340/573.1 |
| 7,770,782 B2 * | 8/2010 | Sahud | 235/375 |
| 8,482,406 B2 * | 7/2013 | Snodgrass | 340/539.12 |
| 2007/0273499 A1 | 11/2007 | Chlubek et al. | |
| 2008/0209665 A1 | 9/2008 | Mangiardi | |
| 2009/0276239 A1 | 11/2009 | Swart et al. | |
| 2010/0088107 A1 | 4/2010 | Ur et al. | |
| 2011/0163870 A1 | 7/2011 | Snodgrass | |

OTHER PUBLICATIONS

"Robot Cleaner a 'Game Changer' for Hospital Infection Epidemic", European Cleaning Journal, http://www.europeancleaningjournal.com/magazine/web-articles/latest-news/robot-cleaner-a-game-changer-for-hospital-infetion-epidemic, p. 1 (2012).

(Continued)

*Primary Examiner* — Tai T Nguyen
(74) *Attorney, Agent, or Firm* — Cantor Colburn LLP; Louis Percello

(57) ABSTRACT

Facility sanitization management includes receiving a condition of an individual and determining the condition is on a pre-defined list of conditions, and receiving tracking information indicative of locations in a facility traversed by the individual. The facility sanitization management also includes retrieving, from a first database, at least one solution for eliminating elements of the condition, and retrieving, from a second database, pre-defined structures and materials disposed in the locations, and identifying prescribed cleaning methods for the pre-defined structures and materials. The facility sanitization management further includes creating a clean-up job for each of the locations using the solution and based on the prescribed cleaning methods.

14 Claims, 3 Drawing Sheets

(56) References Cited

OTHER PUBLICATIONS

Infonaut's Software—Hospital Watch Live, http://www.infonaut.ca/software/hospitalwatchlive.html, pp. 1-2 (Copyright 2006-2009).

Bacheldor, "The Hunt for Killer Germs: A Canadian startup is developing a real-time locating system to track and contain hospital infections" RFiD Journal, pages __(2009).

Intellibot HydroBot—Robotic Cleaning Equipment, http://franklincleaningequipment.com/store.asp?pid=34317, pp. 1-2 (2012).

RTLS Solutions for Hospitals, IntelligentInSites; http://www.intelligentinsites.com/solutions/for-hospitals.html, pp. 1-2 (2012).

Kleiner, "Molecular computers act as tiny ID tags", NewScientist, http://www.newscientist.com/article/dn9904-molecular-computers-act-as-tiny-id-tags.html, pp. 1-2 (2006).

A.Anny Leema, et al., "Applying RFID Technology to Construct an Elegant Hospital Environment," IJCSI International Journal of Computer Science Issues, vol. 8, Issue 3, No. 1, pp. 1-5, May 2011.

Maurno, et al, "Wireless Patient Tracking Can Help Halt Contagion, such as the Swine Flu", http://rfid.net/news/164-wireless-patient-tracking-can-help-halt-contagion-such-as-the-swine-flu, pp. 1-8 (2009).

Xenex—The Solution: Product Feautres, [http://www.xenex.com/?page_id=99], p. 1 (Copyright 2009-2011).

\* cited by examiner

FACILITY SANITIZATION MANAGEMENT

CROSS-REFERENCE TO RELATED APPLICATION

This application is a continuation of U.S. patent application Ser. No. 13/554,600, filed Jul. 20, 2012, the disclosure of which is incorporated by reference herein in its entirety.

BACKGROUND

The present invention relates to healthcare, and more specifically, to facility sanitization management.

When an individual enters a location that is accessible to the public, little information may be known concerning his/her health. For example, an individual may exhibit health symptoms though he/she may be unaware of the underlying condition causing these symptoms. For conditions that are highly contagious, it can be critical to the health and safety of others in the vicinity of the individual to ascertain this information as quickly as possible and take immediate action to prevent the spread of infection.

SUMMARY

In accordance with an exemplary embodiment, a method for implementing facility sanitization management is provided. The method includes receiving a condition of an individual and determining the condition is on a pre-defined list of conditions, and receiving tracking information indicative of locations in a facility traversed by the individual. The method also includes retrieving, from a first database, at least one solution for eliminating elements of the condition, and retrieving, from a second database, pre-defined structures and materials disposed in the locations, and identifying prescribed cleaning methods for the pre-defined structures and materials. The method further includes creating a clean-up job for each of the locations using the solution and based on the prescribed cleaning methods.

In accordance with another exemplary embodiment, a computer program product for implementing facility sanitization management is provided. The computer program product includes a storage medium having instructions embodied thereon, which when executed by a computer processor causes the computer processor to implement a method. The method includes receiving a condition of an individual and determining the condition is on a pre-defined list of conditions, and receiving tracking information indicative of locations in a facility traversed by the individual. The method also includes retrieving, from a first database, at least one solution for eliminating elements of the condition, and retrieving, from a second database, pre-defined structures and materials disposed in the locations, and identifying prescribed cleaning methods for the pre-defined structures and materials. The method further includes creating a clean-up job for each of the locations using the solution and based on the prescribed cleaning methods.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

DETAILED DESCRIPTION

According to exemplary embodiments, facility sanitization management is provided. The facility sanitization management provides the ability to dynamically track locations visited by individuals with known or suspected conditions for the purpose of implementing timely clean-up processes for the affected locations based on the nature of the conditions. The facility sanitization management directs clean-up processes to prevent the spread of infectious disease or other outbreak. In one exemplary embodiment, the facility sanitization management monitors locations visited by individuals using a tracking mechanism and once a condition is determined, the facility sanitization management creates a clean-up job targeted for the specific locations. In another exemplary embodiment, the facility sanitization management collects information concerning locations likely visited by individuals when no tracking mechanism is available, and creates a clean-up job targeted for these locations. These and other features of the facility sanitization management will now be described.

Figure 1:
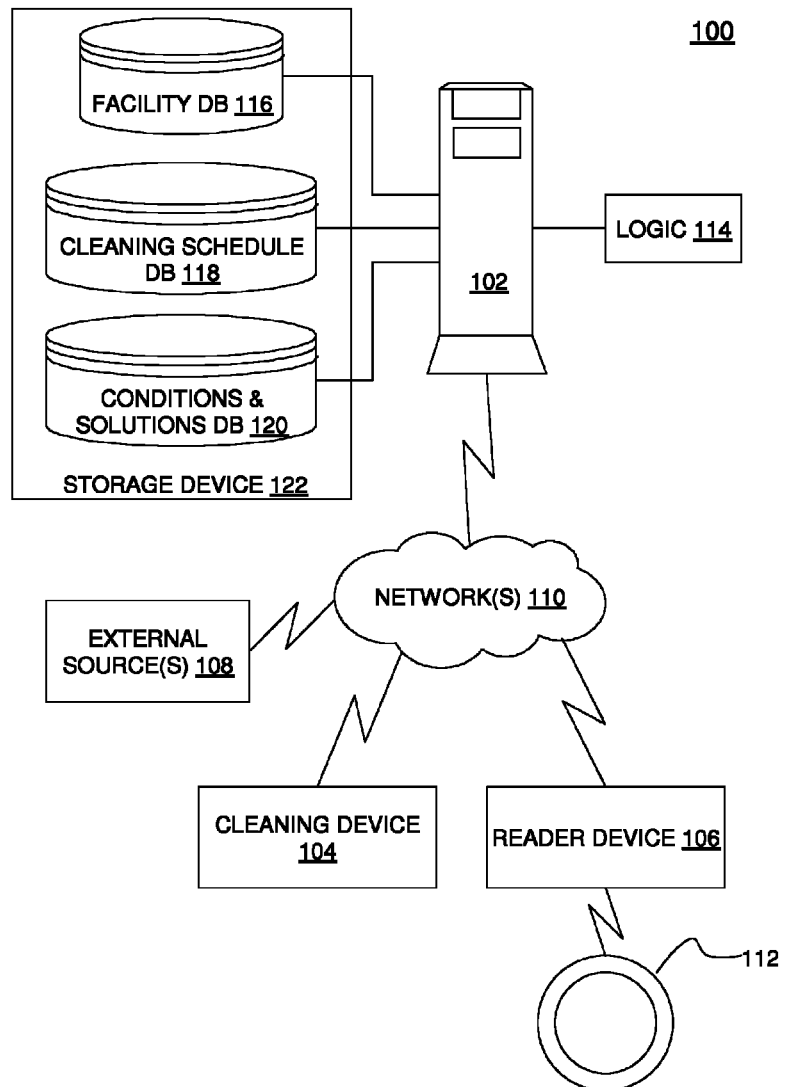
FIG. 1 depicts a block diagram of a system upon which facility sanitization management may be implemented according to an embodiment of the present invention.

Turning now to FIG. 1, a system 100 upon which the facility sanitization management may be implemented will now be described in an exemplary embodiment. The system 100 of FIG. 1 includes a host system 102 in communication with a cleaning device 104, a reader device 106, and external sources 108 over one or more networks 110.

The host system 102 may be implemented as a high-speed computer processing device (e.g., a mainframe computer) that is capable of handling a large volume of activities conducted by users of the facility sanitization management. The host system 102 may be implemented by a medical facility (e.g., a hospital), or any establishment that renders medical services to individuals (e.g., a cruise ship company, a military base, a college university, or a prison, to name a few). It will be understood that the exemplary embodiments may be extended to offer facility sanitization management to non-medical facilities, such as any establishment that comes in contact with the public (e.g., restaurants, manufacturing plants, etc.). Alternatively, the facility sanitization management may be administered by an application service provider (ASP) entity that provides the services to other establishments. In an exemplary embodiment, the host system 102 executes logic 114 for implementing the facility sanitization management described herein.

The cleaning device 104 may include an automated cleaning system. While only a single cleaning device 104 is shown in FIG. 1, it will be understood that any number of cleaning devices 104 may be employed by the facility of the host system 102 in order to realize the advantages of the exemplary embodiments described herein. For example, if the establishment is a hospital, there may be one cleaning device 104 assigned to each room on a floor or each floor in the facility.

It will be understood that the facility itself may be a single structure (e.g., one building) or may include multiple structures and their surrounding areas (e.g., a military base or college campus).

In one embodiment, multiple cleaning devices 104 performing differing functions may be employed. For example, one cleaning device 104 may be a dedicated, stationary device that is configured to perform a specific function (e.g., sterilization of medical instruments), while another cleaning device 104 may include components configured to sanitize floors. Thus, the particular components of the cleaning device 104 may depend on its designated function(s). The cleaning device 104 may include wheels for remote control of the movement of the cleaning device 104. Other components may include one or more of a wireless antenna, a control unit, motor, spray nozzle, cleaning fluid reservoir, laser unit, vacuum inlet, brushes, and sterile, disposable cartridges, to name a few.

As indicated above, one exemplary embodiment of the facility sanitization management utilizes a tracking mechanism to monitor locations visited by an individual. The tracking mechanism includes the reader device 106 and a tracking device 112. The reader device 106 may be any type of wireless tracking system, such as a radio frequency identification (RFID) reader. In this embodiment, an individual (e.g., a patient) is provided with a patient bracelet or medical card having an RFID tag embedded thereon. For purposes of illustration, the tracking device of FIG. 1 is a patient bracelet 112 communicatively coupled to the reader device 106. While only a single reader device 106 is shown in FIG. 1, the embodiments herein are not so limited. For example, there may be many reader devices 106 disposed in locations throughout the facility.

If the tracking system employs RFID technology, the patient bracelet 112 or other device (e.g., a medical card) may include a control module and an antenna. The control module, in turn, may include a processor or logic controller, a modulator, a demodulator, a receiver, a transmitter, and a ground unit. The antenna may be a ferrite core antenna or any suitable antenna used in radio frequency transmissions.

In an alternative embodiment, the tracking system may be implemented using a wireless, global positioning system-enabled communications device, such as a smart phone. In this embodiment, the individual may be tracked using signals received from the communications device indicative of coordinates for the location in which the individual is situated using, e.g., cellular, WiFi, Bluetooth® and/or other wireless communication protocols.

In an embodiment, the external sources 108 may be information sources that provide up-to-date data on infectious diseases or other risks. For example, the external sources 108 may include searchable databases implemented by the World Health Organization (WHO), Centers for Disease Control (CDC), and Occupational Safety and Health Administration (OSHA), or may be a news feed that provides current information on a discovered health risk. In another embodiment in which the tracking mechanism (reader device 106 and bracelet 112) is not employed, the external sources 108 may include databases accessed by the host system 102 in assessing locations of the facility likely visited by an individual over a period of time (e.g., if the facility is a university, the databases may store class schedules and dormitory assignments). The host system 102 may communicate with these external sources 108 over one or more networks 110.

In an exemplary embodiment, the host system 102 is communicatively coupled to a storage device 122 that houses various databases used in implementing the facility sanitization management. The databases include a facility database 116, a cleaning schedule database 118, and a conditions database 120.

The facility database 116 stores particular information relating to the facility subject to the facility sanitization management. In an exemplary embodiment, the facility database 116 is created by users of the host system 102 using, e.g., a user interface provided by the logic 114. For example, the facility database 116 may store user-defined identifiers for areas, structures within the areas, and materials associated with the structures. In addition, the facility database 116 may be configured by a user to store identifiers of one or more cleaning devices 104 and one or more reader devices 106 that are assigned by the user to areas of the facility. For example, a sample data structure used in implementing the facility database is shown as follows:

Area_ID
Structure_ID
Material_ID
Clean_Device_ID
Reader_ID

The area may be defined as a floor, a room, a portion of a room, or a combination thereof. For example, one area identifier may be assigned to a patient waiting room. If the facility includes multiple buildings, the data structure may also include another field for building identifiers. It will be understood that multiple reader devices 106 and/or multiple cleaning devices 104 may be assigned to a single area depending on the needs of the facility.

The cleaning schedule database 118 stores a listing of routine cleaning services performed for the facility broken down by area. The listing of cleaning services may also include a frequency of cleaning (e.g., once per week, daily, etc.). There may be multiple procedures scheduled for each area where each procedure represents a particular task (e.g., damp mop floor, dust surfaces, empty bins, etc.). In one embodiment, the cleaning services may also include one or more types of solutions to be used in each procedure based on the function associated with the area. For example, in a laboratory room in which samples of patient's blood are taken, the solutions may require a fluid that includes a percentage of alcohol or bleach sufficient to eliminate any potential organisms that may be found in blood residue that is inadvertently left on a structure in the area. Thus, if an area is associated with a function that may result in contamination of the area, the cleaning services may specify particular tasks or procedures.

In an exemplary embodiment, the logic 114 is configured to enable access of the cleaning schedule database 118 when creating a clean-up job to identify routine cleaning procedures and associated solutions. The logic 114 may select from these solutions based on a given condition identified for a location in the facility, as will be described further herein.

The conditions database 120 stores conditions indicative of various health risks, along with associated solutions designed to eliminate elements of the condition within a contaminated area. For example, the conditions database 120 may store a listing of infectious diseases and any substances or techniques known for treating contaminated areas based on the type of material or surface that requires cleaning. Examples of substances may include ultraviolet rays, phenol, chemical wash, and anti-bacterial sanitizer, to name a few. The form of application of such substances may also be configured via the logic 114. For example, the form of application may include spray, scrub, soak, etc.

The storage device 122 may be directly in communication with the host system 102 (e.g., via cabling) or may be logically addressable by the host system 102, e.g., as a consolidated data source over one or more networks 110.

The networks 110 may include any type of networks, such as local area networks, wide area networks, virtual private networks, and the Internet. In addition, the networks 110 may be configured to support wireless communications, e.g., via cellular networks, satellite networks, global positioning systems, and short-range wireless communications, such as WiFi and Bluetooth.

Figure 2:
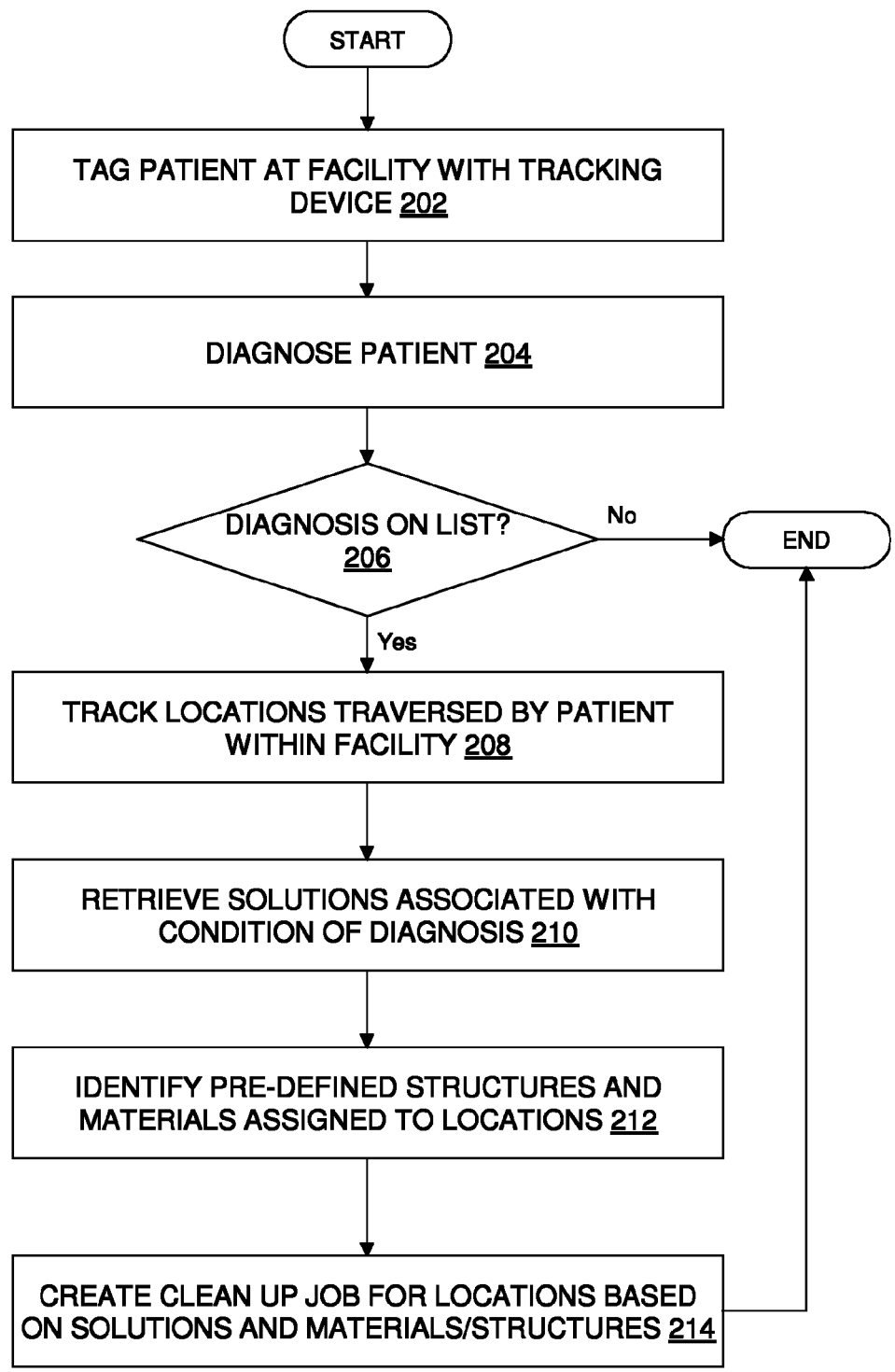
FIG. 2 depicts a flow diagram describing a process for implementing facility sanitization management according to an embodiment of the present invention.

Turning now to FIG. 2, a flow diagram describing a process for implementing the facility sanitization management using the tracking mechanism (e.g., reader device 106 and tracking device 112) will now be described in an exemplary embodiment. For purposes of non-limiting illustration, the process described in FIG. 2 relates to medical facility. In addition, the process of FIG. 2 assumes that an individual (patient) has entered the facility of the system 100 of FIG. 1.

At step 202, the patient is tagged with a tracking device (e.g., bracelet 112). The tracking device may be programmed to store a patient identifier that is mapped to a back-end patient database (not shown) of the host system 102.

At step 204, the patient is diagnosed, or preliminarily diagnosed (e.g., based on symptoms presented), with a disease (also referred to herein as a condition). The diagnosis may be stored in a patient record with the patient identifier in the patient database. At step 206, the logic 114 determines whether the disease is on the list stored in the conditions database 120. For example, the list of diseases may include those are considered at risk for spread or infection.

If the disease is not on the list, this means it is not considered a risk to other individuals in the facility, and the process ends. Otherwise, if the disease is on the list at step 206, the logic 114 tracks locations within the facility visited by the patient at step 208. As indicated above, this tracking may be implemented using RFID technologies in which the reader device(s) 106 communicate with the tracking device (e.g., bracelet 112), and sends this information (e.g., reader identifier(s) and patient identifier) to the host system 102. The logic 114 accesses the facility database 118 and determines the location(s) visited using this information from the reader device(s) 106.

At step 210, the logic 114 uses the condition, or disease information to search the conditions database 120 for a solution configured to decontaminate the locations. At step 212, the logic 114 identifies structures and materials associated with the locations visited by the patient. This identification is performed by searching facility database using identifiers of the areas and/or reader devices 106 ascertained in step 208 and retrieving the associated structure and material information. The structures and materials associated with the locations may impact how the areas are treated. For example, a tile flooring may be scrubbed using a fluid solution, while a fabric covered patient chair may be sprayed using a different solution and/or applicator.

Figure 3:
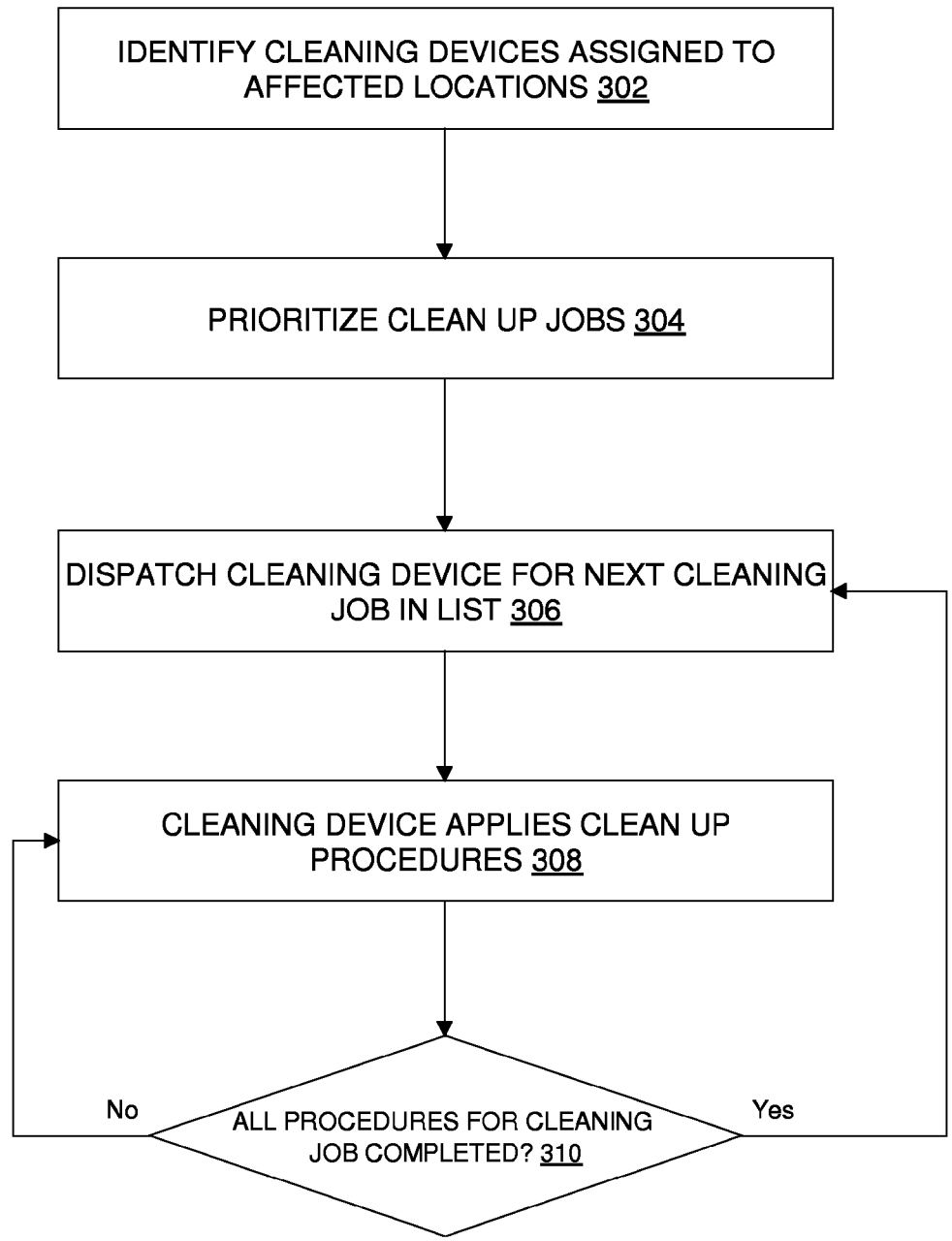
FIG. 3 depicts a flow diagram describing a process for implementing facility sanitization according to another embodiment of the present invention.

At step 214, the logic 114 creates one or more clean-up jobs for the identified locations based on the selected solutions and structures/materials. In one embodiment, the logic 114 may be configured to prioritize procedures for a clean-up job as well as the clean-up jobs themselves. Turning now to FIG. 3, a process for creating and scheduling a clean-up job via the logic 114 will now be described.

In some situations, it may be necessary to create multiple clean-up jobs based on the severity of the contamination and/or the severity of the condition. The logic 114 may be configured to prioritize clean-up jobs based on a priority value assigned to a condition or location of the contamination. The priority value may indicate that a clean-up must be performed immediately. Other priority values may provide an ordering of the clean-up jobs based on the severity of the condition or the severity of the spread of the condition. For example, suppose that a patient with a highly-infectious disease enters a patient waiting room and then subsequently enters an area in which immune-deficient patients (e.g., infants or elderly) are located. The logic 114 may be configured to assign a highest priority to the area in which the immune-deficient patients are located; thus, the priority is assigned based on a perceived health threat to a population of patients. Alternatively, or in conjunction therewith, the priority may be assigned based on the average volume of patients that visit a particular area each day, whereby areas known to have higher traffic than other areas may be given higher priority to a clean-up schedule than low traffic areas.

At step 302, the logic 114 identifies the cleaning device(s) 104 assigned to the affected locations (e.g., via the facility database 116 and area identifiers). At step 304, the logic 114 assigns priority values to each of the clean-up jobs. At step 306, the logic 114 dispatches the cleaning device(s) 104 for the clean-up job at the top of the priority list. At step 308, the cleaning device(s) 104 applies a clean-up procedure as indicated in the clean-up job (e.g., scrub floor, sanitize hospital instruments, etc.). At step 310, the logic 114 determines if all procedures for the first clean-up job(s) have been completed (e.g., by a signal received from the cleaning device 104). If not, the process returns to step 308. Otherwise, the process returns to step 306.

In addition to scheduling clean-up jobs, the logic 114 may be configured to determine and implement a quarantine plan of action based on the nature of the condition. For example, information from the external sources 108 (e.g., news feed) may provide information as to the location of a detected condition or outbreak. Another external source 108 (e.g., WHO database) may indicate a safe distance from a location of the condition in which individuals must maintain in order to prevent infection. For example, suppose the distance is 10 meters. The logic 114 may alert patients, staff, or other individuals (e.g., through existing intercom systems) who are located inside of this distance to remain in their current location to prevent further outbreaks.

As indicated above, the facility sanitization management may be employed without the reader device 106 and tracking device 112. In this embodiment, when an individual is found to be contagious, the logic 114 uses personal information of the individual (e.g., name, social security number, etc.) to search one or more databases (e.g., if the facility is a military base, the databases 108 may store barracks assignments, as well as a work location of the individual). A 'most-likely-traveled path' may be derived from this information, and a clean-up job may be created for treating these areas.

Technical effects of the invention provide the ability to dynamically track individuals with known or suspected conditions for the purpose of implementing timely clean-up processes for affected locations based on the nature of the conditions. The facility sanitization management directs clean-up processes to prevent the spread of infectious disease or other outbreak. The facility sanitization management monitors locations visited by individuals using a tracking mechanism and once a condition is determined, the facility sanitization management creates a clean-up job targeted for the specific locations.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

What is claimed is:

1. A method, comprising:
   receiving a condition of an individual and determining the condition is on a pre-defined list of conditions;
   receiving, at a computer processor, tracking information indicative of locations in a facility traversed by the individual, the locations monitored via a tracking device associated with the individual;
   retrieving, from a first database, at least one solution for eliminating elements of the condition;
   retrieving, from a second database, pre-defined structures and materials disposed in the locations, and identifying prescribed cleaning methods for the pre-defined structures and materials; and
   creating a clean-up job for each of the locations using the at least one solution and based on the prescribed cleaning methods.

2. The method of claim 1, wherein the condition is an infectious disease.

3. The method of claim 1, wherein the tracking device includes at least one of:
   a medical bracelet embedded with an antenna and a microchip; and
   a medical card embedded with an antenna and a microchip;
   wherein the tracking device wirelessly communicates with at least one reader device disposed in at least one of the locations, the computer processor receiving the tracking information from the at least one reader device.

4. The method of claim 1, wherein the tracking device includes a global positioning system-enabled communication device;
   wherein the computer processor receives the location information from coordinates provided via the global positioning system-enabled communication device.

5. The method of claim 1, wherein the creating a clean-up job for each of the locations includes:
   calculating a risk value for the condition with respect to each of the locations;
   assigning a priority value to each of the clean-up jobs based on the priority value; and
   dispatching at least one automated cleaning device based on the priority value.

6. The method of claim 1, further comprising:
   assigning an identifier of an automated cleaning device to a defined area of the facility; and
   storing the identifier in the second database;
   wherein creating the clean-up job includes scheduling the automated cleaning device for the clean-up job when the defined area is within at least one of the locations.

7. The method of claim 1, wherein the structures include at least one of furniture, flooring, walls, sinks, showers, vents, and equipment.

8. A computer program product comprising a non-transitory storage medium having instructions embodied thereon, which when executed by a computer processor, causes the computer processor to implement a method, the method comprising:
   receiving a condition of an individual and determining the condition is on a pre-defined list of conditions;
   receiving tracking information indicative of locations in a facility traversed by the individual, the locations monitored via a tracking device associated with the individual;
   retrieving, from a first database, at least one solution for eliminating elements of the condition;
   retrieving, from a second database, pre-defined structures and materials disposed in the locations, and identifying prescribed cleaning methods for the pre-defined structures and materials; and
   creating a clean-up job for each of the locations using the at least one solution and based on the prescribed cleaning methods.

9. The computer program product of claim 8, wherein the condition is an infectious disease.

10. The computer program product of claim 8, wherein the tracking device includes at least one of:
    a medical bracelet embedded with an antenna and a microchip; and
    a medical card embedded with an antenna and a microchip;
    wherein the tracking device wirelessly communicates with at least one reader device disposed in at least one of the locations, the computer processor receiving the tracking information from the at least one reader device.

11. The computer program product of claim 8, wherein the tracking device includes a global positioning system-enabled communication device;
    wherein the computer processor receives the location information from coordinates provided via the global positioning system-enabled communication device.

12. The computer program product of claim 8, wherein the creating a clean-up job for each of the locations includes:
    calculating a risk value for the condition with respect to each of the locations;
    assigning a priority value to each of the clean-up jobs based on the priority value; and
    dispatching at least one automated cleaning device based on the priority value.

13. The computer program product of claim 8, wherein the method further comprises:
    assigning an identifier of an automated cleaning device to a defined area of the facility; and
    storing the identifier in the second database;
    wherein creating the clean-up job includes scheduling the automated cleaning device for the clean-up job when the defined area is within at least one of the locations.

14. The computer program product of claim 8, wherein the structures include at least one of furniture, flooring, walls, sinks, showers, vents, and equipment.

* * * * *